United States Patent
Li et al.

(10) Patent No.: US 9,869,628 B2
(45) Date of Patent: Jan. 16, 2018

(54) METHODS OF COLLECTING CELLS FROM MULTI-WELL PLATES FOR USE IN FLOW CYTOMETRY

(71) Applicant: ACEA Biosciences, Inc., San Diego, CA (US)

(72) Inventors: Nan Li, San Diego, CA (US); Sean Lee, San Diego, CA (US); Kilo Vilayphone, San Diego, CA (US); Xiaobo Wang, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 0 days.

(21) Appl. No.: 14/750,613

(22) Filed: Jun. 25, 2015

(65) Prior Publication Data

US 2016/0097707 A1    Apr. 7, 2016

Related U.S. Application Data

(60) Provisional application No. 62/017,251, filed on Jun. 25, 2014.

(51) Int. Cl.
    *G01N 15/14* (2006.01)
    *G01N 15/10* (2006.01)

(52) U.S. Cl.
    CPC . *G01N 15/1404* (2013.01); *G01N 2015/1006* (2013.01); *G01N 2015/1486* (2013.01)

(58) Field of Classification Search
    None
    See application file for complete search history.

(56) References Cited

U.S. PATENT DOCUMENTS

| | | | |
|---|---|---|---|
| 4,482,994 A | 11/1984 | Ishikawa | |
| 4,573,796 A | 3/1986 | Martin | |
| 4,707,064 A | 11/1987 | Dobrowolski | |
| 5,674,698 A | 10/1997 | Zarling et al. | |
| 5,760,900 A | 6/1998 | Ito et al. | |
| 5,865,520 A | 2/1999 | Kavanagh et al. | |
| 5,930,048 A | 7/1999 | Kaneko | |
| 6,294,063 B1 * | 9/2001 | Becker | B01F 13/0076 204/450 |
| 6,404,493 B1 | 6/2002 | Altendorf | |
| 6,558,945 B1 | 5/2003 | Kao | |
| 7,110,192 B2 | 9/2006 | Sauter et al. | |
| 7,738,099 B2 | 6/2010 | Morrell | |
| 7,758,811 B2 | 7/2010 | Durack et al. | |
| 7,777,869 B2 | 8/2010 | Nerin | |
| 7,952,806 B2 | 5/2011 | Callen | |
| 8,077,310 B2 | 12/2011 | Olson | |
| 8,101,426 B2 | 1/2012 | Durack | |
| 8,619,370 B2 | 12/2013 | Hunter et al. | |
| 8,883,495 B2 | 11/2014 | Nakamura et al. | |
| 9,158,118 B2 | 10/2015 | Li et al. | |
| 2007/0096039 A1 | 5/2007 | Kapoor | |
| 2009/0141327 A1 | 6/2009 | Penn | |
| 2010/0322064 A1 * | 12/2010 | Kim | G01N 21/6428 369/126 |
| 2013/0200277 A1 | 8/2013 | Li et al. | |
| 2015/0140577 A1 | 5/2015 | Li et al. | |

FOREIGN PATENT DOCUMENTS

| | | |
|---|---|---|
| WO | 2003/021241 A1 | 3/2003 |
| WO | 2011/003073 A1 | 1/2011 |

OTHER PUBLICATIONS

Ramirez et al. "High-throughput flow cytometry: validation in microvolume bioassays", Cytometry Part A 53A: 55-65, 2003.*
Scientiis International "Corning and Costar 96-well cell culture plates" available on the company's webpage for product information, copyright 2005.*
PCT/US2014/066429 International Search Report and Written Opinion dated Mar. 23, 2015.
EP12845835.3 European Search Report dated Jul. 1, 2015.
EP12841762.3 Extended European Search Report dated Mar. 27, 2015.

* cited by examiner

*Primary Examiner* — Emily Cordas
(74) *Attorney, Agent, or Firm* — Wagenknecht IP Law Group PC

(57) ABSTRACT

A method of collecting cells from individual wells of a multi-well plate for use in flow cytometry, the method including adding a suspension of cells to wells of the multi-well plate; and aspirating cells from different wells according to a collection pattern into a flow cytometer, wherein the collection pattern is a sequential ordering of wells beginning at a middle region of the multi-well plate and continuing towards an outer region of the multi-well plate. The method preferably including rotating or agitating the multi-well plate between steps of aspirating cells from different wells. Exemplary collection patterns include spiral-square collection pattern and a nearest well to center collection pattern.

18 Claims, 7 Drawing Sheets

|   | 1 | 2 | 3 | 4 | 5 | 6 | 7 | 8 | 9 | 10 | 11 | 12 |
|---|---|---|---|---|---|---|---|---|---|---|---|---|
| A | 66 | 65 | 43 | 42 | 41 | 40 | 39 | 38 | 37 | 64 | ■ | 95 |
| B | 67 | 68 | 44 | 21 | 20 | 19 | 18 | 17 | 36 | 63 | 93 | 94 |
| C | 70 | 69 | 45 | 22 | 7 | 6 | 5 | 16 | 35 | 62 | 92 | 91 |
| D | 71 | 72 | 46 | 23 | 8 | [1] | 4 | 15 | 34 | 61 | 89 | 90 |
| E | 74 | 73 | 47 | 24 | 9 | 2 | 3 | 14 | 33 | 60 | 88 | 87 |
| F | 75 | 76 | 48 | 25 | 10 | 11 | 12 | 13 | 32 | 59 | 85 | 86 |
| G | 78 | 77 | 49 | 26 | 27 | 28 | 29 | 30 | 31 | 58 | 84 | 83 |
| H | 79 | 80 | 50 | 51 | 52 | 53 | 54 | 55 | 56 | 57 | 81 | 82 |

FIG. 1

|   | 1 | 2 | 3 | 4 | 5 | 6 | 7 | 8 | 9 | 10 | 11 | 12 |
|---|---|---|---|---|---|---|---|---|---|----|----|----|
| A | 93 | 85 | 69 | 53 | 52 | 38 | 37 | 51 | 60 | 72 | 88 | ■ |
| B | 92 | 76 | 54 | 44 | 29 | 20 | 19 | 28 | 43 | 59 | 73 | 89 |
| C | 84 | 68 | 45 | 30 | 14 | 6 | 5 | 13 | 27 | 50 | 65 | 81 |
| D | 77 | 61 | 39 | 21 | 7 | 1 | 4 | 12 | 18 | 36 | 64 | 80 |
| E | 78 | 62 | 40 | 22 | 8 | 2 | 3 | 11 | 17 | 35 | 63 | 79 |
| F | 83 | 67 | 46 | 31 | 15 | 9 | 10 | 16 | 26 | 49 | 66 | 82 |
| G | 91 | 75 | 55 | 41 | 32 | 23 | 24 | 25 | 42 | 58 | 74 | 90 |
| H | 94 | 86 | 70 | 56 | 47 | 33 | 34 | 48 | 57 | 71 | 87 | 95 |

| Well | 1 | 2 | 3 | 4 | 5 | 6 | 7 | 8 | 9 | 10 | 11 | 12 | Avg. | St. Dev. | CV |
|---|---|---|---|---|---|---|---|---|---|---|---|---|---|---|---|
| A | | 901 | 884 | 822 | | 802 | 858 | 848 | 809 | 849 | 848 | 834 | 780 | 248.2 | 0.31 |
| B | 867 | 878 | 806 | 810 | 888 | 797 | 762 | 806 | 867 | 844 | 920 | 876 | 825 | 61.4 | 0.07 |
| C | 873 | 769 | 825 | 879 | 827 | 812 | 807 | 782 | 836 | 791 | 842 | 821 | 822 | 33.2 | 0.04 |
| D | 875 | | 806 | 794 | 770 | | | | | | | | 787 | 47.2 | 0.05 |
| E | 803 | 676 | 831 | 751 | 783 | 740 | 750 | 799 | 751 | 791 | 826 | 850 | 796 | 43.5 | 0.05 |
| F | 884 | 856 | 795 | 803 | 780 | 747 | 833 | 815 | 779 | 827 | 861 | 821 | 816 | 38.9 | 0.04 |
| G | 905 | 671 | 843 | 762 | 782 | 792 | 773 | 769 | 831 | 794 | 892 | 717 | 810 | 57.4 | 0.07 |
| H | 841 | | | | 869 | | | | | | | 663 | 831 | 54.9 | 0.06 |
| Avg. | 870 | 853 | 828 | 813 | 687 | 779 | 797 | 799 | 810 | 813 | 858 | 798 | | Total Plate Average: 818 | |
| STD | 31.5 | 39.9 | 28.1 | 44.6 | 282.4 | 44.8 | 39.6 | 33.8 | 46.3 | 32.1 | 32.1 | 71.7 | | | |
| CV | 0.03 | 0.04 | 0.03 | 0.05 | 0.41 | 0.05 | 0.04 | 0.04 | 0.05 | 0.03 | 0.03 | 0.08 | | | |

FIG. 7

METHODS OF COLLECTING CELLS FROM MULTI-WELL PLATES FOR USE IN FLOW CYTOMETRY

CROSS-REFERENCE TO RELATED APPLICATIONS

This application claims the benefit of priority under 35 U.S.C. §119(e) of U.S. Ser. No. 62/017,251, filed Jun. 25, 2014; the content of which is herein incorporated by reference in its entirety.

FIELD OF THE INVENTION

The invention relates generally to the field of flow cytometry and more specifically to methods of sample collection from multi-well plates for use with flow cytometry systems.

BACKGROUND OF THE INVENTION

Flow cytometry is a laser-based, biophysical technology where fluorescent molecules coupled to cells are aspirated into the flow cytometer, then passed one by one through a flow cell and excited by a set of lasers. The emitted fluorescence is then collected and transformed into an electrical signal for analysis. Labelling cells with molecules that fluoresce at different wavelengths allows the user to identify a variety of distinct cell populations and therefore it provides a powerful tool with diagnostic, therapeutic, and research applications. For example, the technique is often used to count cells from a biological sample, such as counting CD4/CD8 populations from circulating blood in human immunodeficiency virus (HIV) studies to map the disease, and to sort cells from a mixed population of cells, such as stem cell sorting from harvested biological samples for possible differentiation and reintroduction into different areas of the patient's body.

Since numerous distinct cell populations can be identified using flow cytometry often a single flow cytometry experiment or test includes a large number of samples. Therefore, there is a need to increase the throughput of flow cytometers. One solution is to present test samples on multi-well plates and program a robot to acquire samples across the multi-well plates, which is conventionally performed by aspirating cell samples from the wells. However, a challenge with presenting cells in multiwall plates is that cells tend to settle from solution and collect at the bottom of wells while waiting for aspiration, thereby decreasing cell yields in later aspirated samples.

A possible solution to the problem of cell settling is to rotate or agitate multi-well plates at various intervals to assist in suspending cells for aspiration. We attempted different intervals including between steps of aspirating samples from different wells. However, it has now been found that merely using a conventional suspension approach of rotating or agitating the multi-well plate, even at frequent intervals, only significantly helps suspend cells positioned at opposing ends of the plate. Importantly, it is found to be insufficient to suspend cells positioned within the middle region of the plates. That is, the approach tends to suspend cells in the outer region of the multi-well plate but fails to adequately suspend cells at the middle region of the plate. Accordingly, there is a need to develop an approach useful in high throughput sample acquisition for flow cytometry procedures that can increase the consistency of cell yields across the entire multiwall plate.

BRIEF SUMMARY OF THE INVENTION

The above deficiencies in sample acquisition are addressed by the methods of the invention. More specifically, the methods accomplish at least two objectives related to high throughput sampling of multi-well plates in flow cytometry applications. The first is to improve consistency of particle or cell counts across the entirety of the plate. The second is to alleviate the issue of inconsistent mixing across the plate by agitation or plate shaking.

The above is achieved through a method of collecting cells from individual wells of a multi-well plate for use in a flow cytometry applications, which includes adding a suspension of cells to the wells of the multi-well plate; and aspirating cells from different wells according to a collection pattern into a flow cytometer, where the collection pattern is a sequential ordering of wells beginning at a middle region of the multi-well plate and continuing towards an outer region of the multi-well plate. In preferred embodiments the method further includes rotating or agitating the multi-well plate between steps of aspirating cells from different wells.

The method is useful for any cell or particle suitable for flow cytometry systems. Typically cells or particles will be sized between 0.2 µm to 150 µm and the methods will become still more useful as cells tend to settle from solution at higher rates. The method can be used with prokaryotic cells but is preferably used with eukaryotic cells and in particular human cells. To this end, the method can be used when detecting, counting or sorting any cell or particle population consistent with flow cytometry systems including cancer cells, monocytes, lymphocytes, and other cells isolated from tissue or grown in cultures sized between 0.2 µm to 150 µm. As known in the flow cytometry arts, the cells may be labelled with one or more labelled binding reagents against one or more cell biomarkers or exposed to one or more detectable intercalating agents. In some embodiments, the labelled binding reagents are fluorescently labelled antibodies or antibody fragments and the intercalating agent is propidium idodide. In other methods the cells are not labelled, such as experiments where only forward scatter (FSC) and side scatter (SSC) data is required.

In preferred embodiments, the multi-well plate is a 96 well plate, characterized as having rows A-H and columns 1-12. Preferably, the middle region is characterized as a well selected from the group consisting of wells D6, D7, E6 and E7. In some embodiments, cells from wells B4-B8, C4-C8, D4-D8, and E4-E8 are aspirated before cells from remaining all wells in a same 96 well plate. Still further, in some embodiments, cells from wells C5-C7, D5-D7, and E5-E7 are aspirated before cells from all remaining wells of a same 96 well plate. In embodiments where two or more plates are provided, the methods may aspirate samples from the above wells from different plates prior to aspirating cells from all remaining wells of the different plates or may aspirate all wells from a same plate prior to aspirating cells from a different plate.

In some embodiments, the collection pattern is a spiral-square configuration, which is characterized as a series of wells in successive square patterns that each circle the middle region and where the sequential ordering proceeds by aspirating adjacent wells. When the multi-well plate is a 96 well plate, the spiral-square configuration can include three successive square patterns around a central well, such as well selected from the group consisting of wells D6, D7, E6 and E7 but preferably D6. In some embodiments, the spiral-square configuration is further characterized as successively aspirating cells from wells that are immediately adjacent to the prior well that was aspirated for at least one half of all wells in the 96 well plate.

In an exemplary embodiment, the multi-well plate is a 96 well plate defined by rows A-H and columns 1-12, and the sequential ordering includes the well order D6, E6, E7, D7, C7, C6, C5, D5, E5, F5, F6, F7, F8, E8, D8, C8, B8, B7, B6, B5, B4, C4, D4, E4, F4, G4, G5, G6, G7, G8, G9, F9, E9, D9, C9, B9, A9, A8, A7, A6, A5, A4, A3, B3, C3, D3, E3, F3, G3, H3, H4, H5, H6, H7, H8, H9, H10, G10, F10, E10, D10, C10, B10, A10. In one variation, the order further includes the order of A2, A1, B1, B2, C2, C1, D1, D2, E2, E1, F1, F2, G2, G1, H1, H2, H11, H12, G12, G11, F11, F12, E12, E11, D11, D12, C12, C11, B11, B12, A12, A11. In another variation, the order further includes meandering or alternating between rows of column 1 and column 2 or rows of column 11 and column 12.

In other embodiments the collection pattern is a nearest well to center pattern, which is characterized as successively aspirating cells from a well that is nearest to the middle region, where the middle region is defined as a center of the multi-well plate independent of whether a well is positioned at the center. A modified nearest well to center is a variation on the embodiment and is characterized as successively aspirating cells from a well that is nearest to both the middle region and a well from which an immediately prior cell was aspirated.

In another exemplary embodiment the multi-well plate is a 96 well plate and the collection order is D6, E6, E7, D7, C7, C6, D5, E5, F6, F7, E8, D8, C8, C5, F5, F8, E9, D9, B7, B6, D4, E4, G6, G7, G8, F9, C9, B8, B5, C4, F4, G5, H6, H7, E10, D10, A7, A6, D3, E3, G4, G9, B9, B4, C3, F3, H5, H8, F10, C10, A8, A5, A4, B3, G3, H4, H9, G10, B10, A9, D2, E2, E11, D11, C11, F11, F2, C2, A3, H3, H10, A10, B11, G11, G2, B2, D1, E1, E12, D12, C12, F12, F1, C1, A2, H2, H11, A11, B12, G12, G1, B1, A1, H1, H12, and A12.

The collection pattern may include two or more distinct patterns. In some embodiments the first pattern is a square pattern or spiral-square pattern and a second pattern is a meandering pattern.

The collection patterns themselves may be programmed by the user into a sample collection or acquisition software module or can be preloaded in flow cytometer as one or more presets, which provides the user with a selectable option to use one or more sample collection patterns. Alternatively, a sample collection module of sample acquisition software may automatically perform the collection patterns. The software may also assign the rotation or shaking interval of the multi-well plate.

In a related embodiment, the invention provides a method of collecting cells from individual wells of a multi-well plate for flow cytometry, the method comprising determining particle or cell counts from each well of the multi-well plate by flow cytometry; ordering the wells from lowest particle count to highest particle count; generating a sequential order for collection that follows the ordering of wells to establish a collection pattern; and collecting particles or cells according to the collection pattern in a second multi-well plate by flow cytometry. In preferred embodiments, the method also includes rotating or agitating the multi-well plate between steps of collecting particles or cells from different wells. In some embodiments the pattern exactly follows the ordering of wells from lowest particle count to highest particle count; however, in other embodiments the collection pattern deviates from the ordering of wells less than 15%.

BRIEF DESCRIPTION OF THE DRAWINGS

Those of skill in the art will understand that the drawings, described below, are for illustrative purposes only. The drawings are not intended to limit the scope of the invention but instead to demonstrate the improvements over the state of the art and various exemplary embodiments.

FIG. 1 is table representing a 96 well plate, which shows a collection pattern including both a spiral—square pattern and a following meandering pattern. An exemplary sequential ordering of each well is demonstrated.

FIG. 2 is table representing a 96 well plate, which shows a collection pattern including a nearest well to center pattern. An exemplary sequential ordering of each well is demonstrated.

FIG. 4 is a table displaying the measured counts of silica particles from each well of a 96 well plate using a row-by-row collection pattern (proceeding from row A to row H) and corresponding statistics.

FIG. 5 is a table displaying the measured counts of silica beads from each well of a 96 well plate using a spiral-square collection pattern and corresponding statistics.

FIG. 6 is a table displaying the measured counts of silica beads using a nearest to center collection pattern, in which the wells are sampled in order based on the nearest distance from the center of the 96 well plate.

FIG. 7 is a table displaying the measured counts per well of polystyrene beads using a spiral-square collection pattern and corresponding statistics.

DETAILED DESCRIPTION OF PREFERRED EMBODIMENTS

Figure 3:
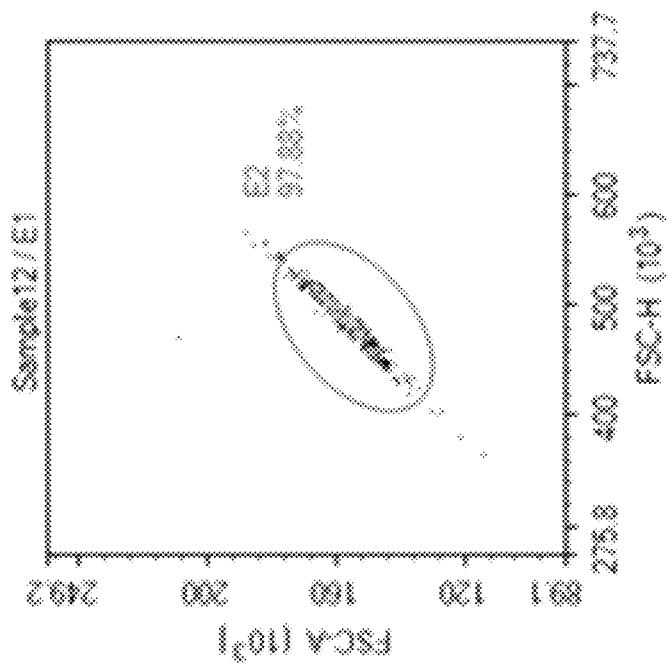
FIG. 3 is a series of flow cytometry plots comparing forward scatter and side scatter for polystyrene beads and gated populations E1 and E2 for well F7 using the collection pattern of FIG. 1.
Figure 3:
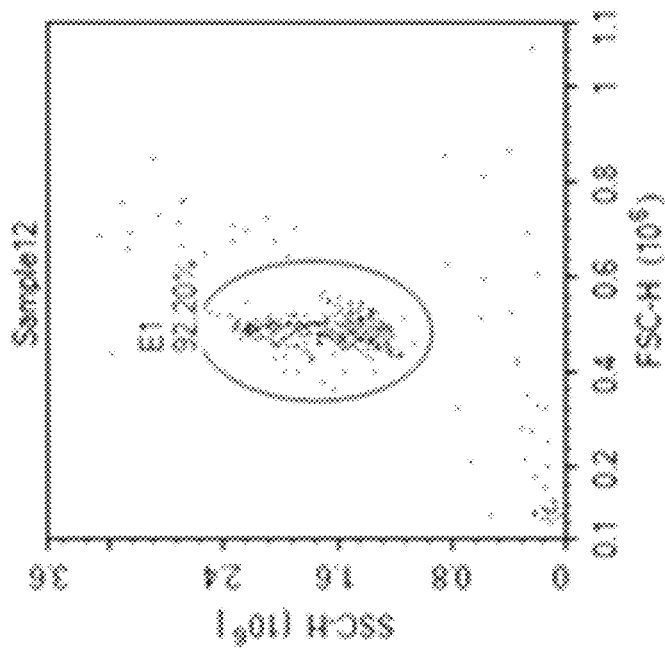

Unless defined otherwise, all technical and scientific terms used herein have the same meaning as commonly understood by one of ordinary skill in the art to which this invention belongs. Although methods and materials similar or equivalent to those described herein can be used in the practice or testing of the invention, the preferred methods and materials are now described. To facilitate understanding of the invention, a number of terms and abbreviations as used herein are defined below as follows.

The term "multi-well plate" as used herein refers to a plate having a plurality of wells capable of retaining a population of cells having a suitable working volume for flow cytometry sample aspiration. Multi-well plates are commonly available in formats of 6 well, 12 well, 24 well, 48 well, 96 well, 384 well and 1536 well and can be flat bottom or rounded bottom. Conventional 6 and 12 well plates have working volumes of about 1.9-2.9 mL and 0.76-1.14 mL respectively and are not typically used for highthroughput flow cytometry. Conventional 48 well plates have a working volume of about 190-285 µL and therefore may be used but are not typically preferred due to the desire to increase the number of available wells thereby increasing throughput. Conventional 96 well plates have a working volume of about 100-200 µL and are preferred as they balance the needs of high throughput with sufficient sample volume for high throughput flow cytometry. Conventional 384 well plates having a working volume of 25-50 µL and may be suitable but much less preferred as the sample volumes are on the low end of flow cytometry applications. 1536 well plates having a working volume of 5-10 µL and are therefore much less desirable. Most preferably, the multi-well plate is a 96 well plate having a rounded bottom.

The term "row-by-row" as used herein refers to a collection pattern that proceeds across a single row, then proceeds across a neighboring row, and so on until all rows are aspirated. In the case of a conventional 96 well plate, cells or particles from wells assigned to column 1-12 of the row "A" are typically aspirated first, followed by the aspiration of cells or particles from wells assigned to columns 1-12 of row "B", then row "C", and so on until aspirating samples from all columns across each row.

The term "column-by-column" as used herein refers to a collection pattern that proceeds up or down a single column, then proceeds up or down the neighboring column and so on. In the case of a 96 well plate, samples from each row of the column conventionally referred to as column "1" are typically aspirated first, followed by the aspiration of cells or particles from each row of column "2", then column "3", and so on until cells are aspirated from all rows of each column.

The term "spiral-square" as used herein is a collection pattern that follows a sequence of successive square patterns in a spiral order. The spiral order can be a right handed spiral or a left handed spiral, which spirals to the right or left.

The term "sequential ordering" as used herein refers to the order of wells for aspiration.

The term "middle region" as used herein refers to the center most point of the multi-well plate together with immediately adjacent wells. Preferably, the middle region is characterized as having four (4) or fewer wells. If there are an even number of rows or columns, such as on a 96 well plate, the middle region can be the combination of wells that form the center of both the rows and columns (e.g. a region defined by D6, D7, E6, and E7 on a 96 well plate), any two of the combination of wells (e.g. a region defined by one of D6 and D7, E6 and E7, D6 and E6, D6 and E7, E6 and E7) or any single well of the combination (e.g. D7, D7, E6, or E7).

The term "continuing towards" as used herein refers to a progression over a series of wells.

The term "successive pattern" as used herein refers a pattern of wells that maintains a prior pattern of wells but differs in size. "Successive square pattern" in a 96 well plate can include a first square pattern formed from wells E5-E7, C7-E7, C5-C7 and C5-E5; followed by a second square pattern formed from wells F4-F8, B8-F8, B4-B8, and B4-F4; and followed by a third square pattern formed from wells G3-G9, A9-G9, A3-A9 and A3-G3.

The term "immediately adjacent" as used herein refers to the positioning of two wells next to one another without an intervening well.

The term "well that is nearest to the center of the multi-well plate and from which an immediately prior cell was aspirated" as used herein to the well that has not yet been aspirated and that compared to remaining wells that have not yet been aspirated has the lowest sum of distances to the both the center of the multi-well plate and to the well from which a sample was last aspirated.

The term "selectable preset" as used herein refers to a software option that encodes the collection pattern that may be selected by a user without additional programming.

The term "biomarker" as used herein refers to a detectable moiety of a cell. A biomarker may be a cluster of differentiation (CD) for a cell, such as a glycoprotein found on a surface of a cell, can be a nucleic acid, or any other moiety useful for detecting one or more cells in flow cytometry.

As an introduction to the invention, among the challenges presented during sample acquisition in high throughput flow cytometry systems that use multi-well plates is maintaining consistent particle or cell counts across all wells of the plate. In particular, as cells wait for aspiration they tend to settle to the bottom of the well. While one of ordinary skill in the art may consider rotating or agitating the plate using a rotating platform or shaking platform, Example I demonstrates this does not adequately suspend cells across the entirety of the multi-well plate. More specifically, Example I and corresponding FIG. 4 demonstrate the need to address inconsistencies in particle count or cell count across different wells of a 96 well plate even when rotating or agitating the multi-well plate.

Figure 4:
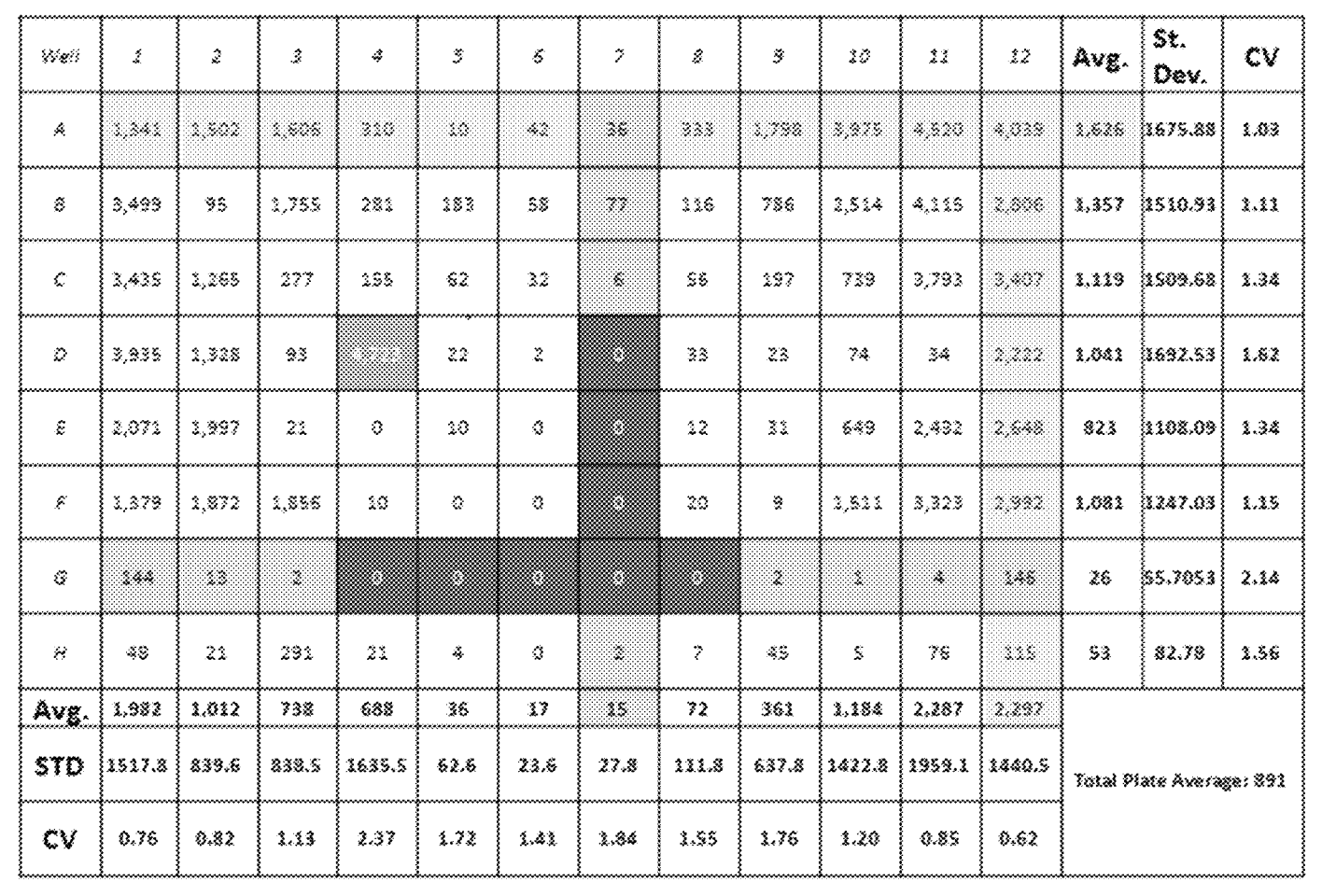

In Example I, cells were added in equal amounts to each well across the multi-well plate. Wells were aspirated, and the plate was rotated or agitated between aspirating each well. The collection pattern used was a conventional a row-by-row sample collection method, where samples were collected across row A before proceeding to row B and so on. There was a significant discrepancy found in particle counts across the wells. That is, particle counts were found to be inconsistent across the plate when using a row-by-row approach even with rotating or agitating the plate after aspirating each well. In particular, as shown in FIG. 4, data collected from wells at about the middle columns of the plate had significantly fewer counts than wells located at end columns. For instance, the average particle counts from columns 1-3 and 10-12 were significantly higher than the average particle counts for columns 4-6 and 7-9. Further, the average particle counts at the middle most columns, namely columns 5-7 were the lowest overall. Still further, aspirates from wells D7, E4, E6, E7, F5-7, and G4-8 did not yield any particle counts. Since middle regions of the plate are shown to benefit the least from rotation or shaking of the multi-well plate, the object of the invention is to devise an approach to increase particle or cell counts at the middle region of the multi-well plate. As to 96 well plates, the primary challenge is to increase counts at wells closest to wells D6, D7, E6 and E7, where plate rotation and agitation alone was found to be the least effective. For completeness, although not shown, column-by column sample collection also suffers from a same problem.

Figure 5:
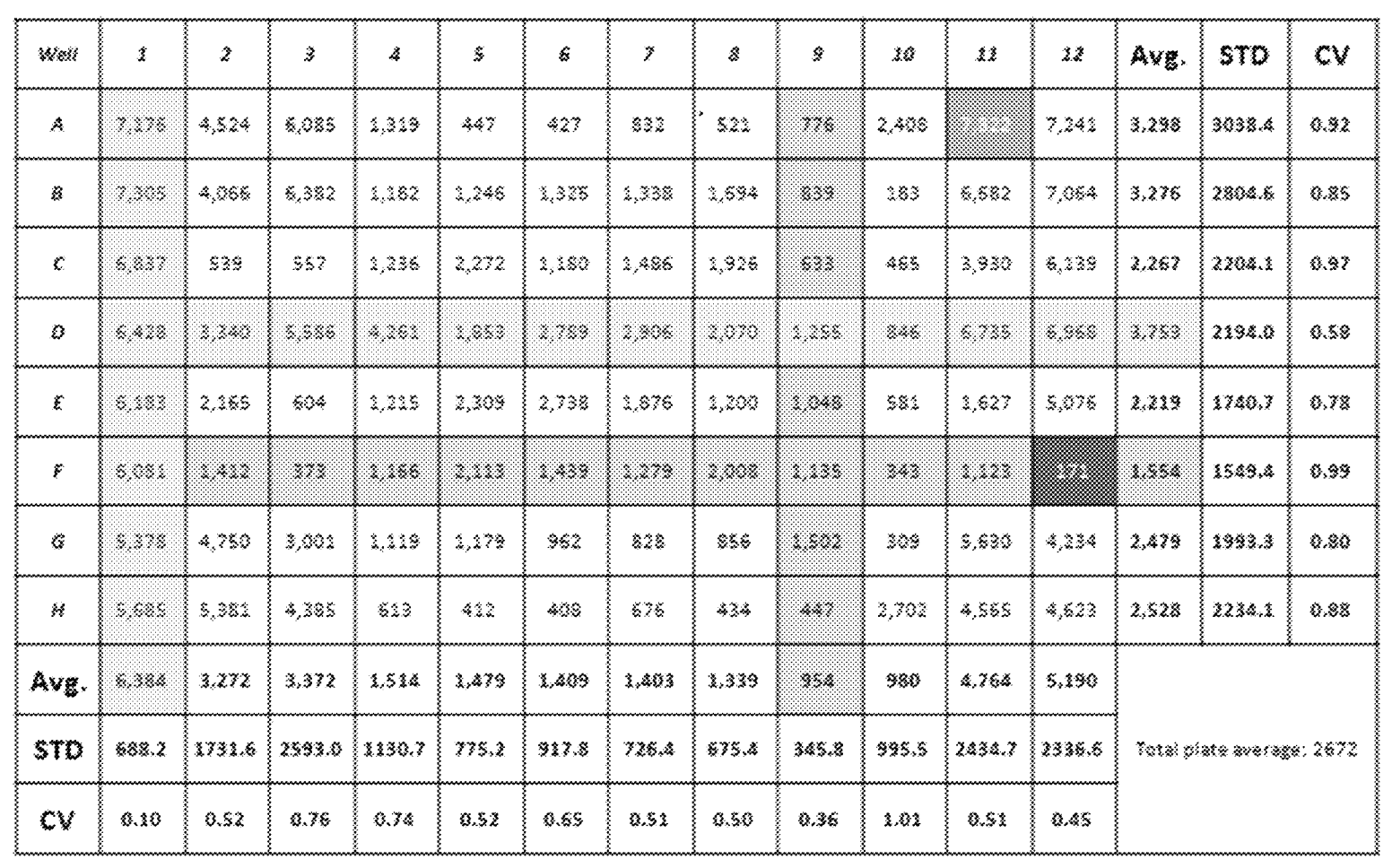
Figure 6:
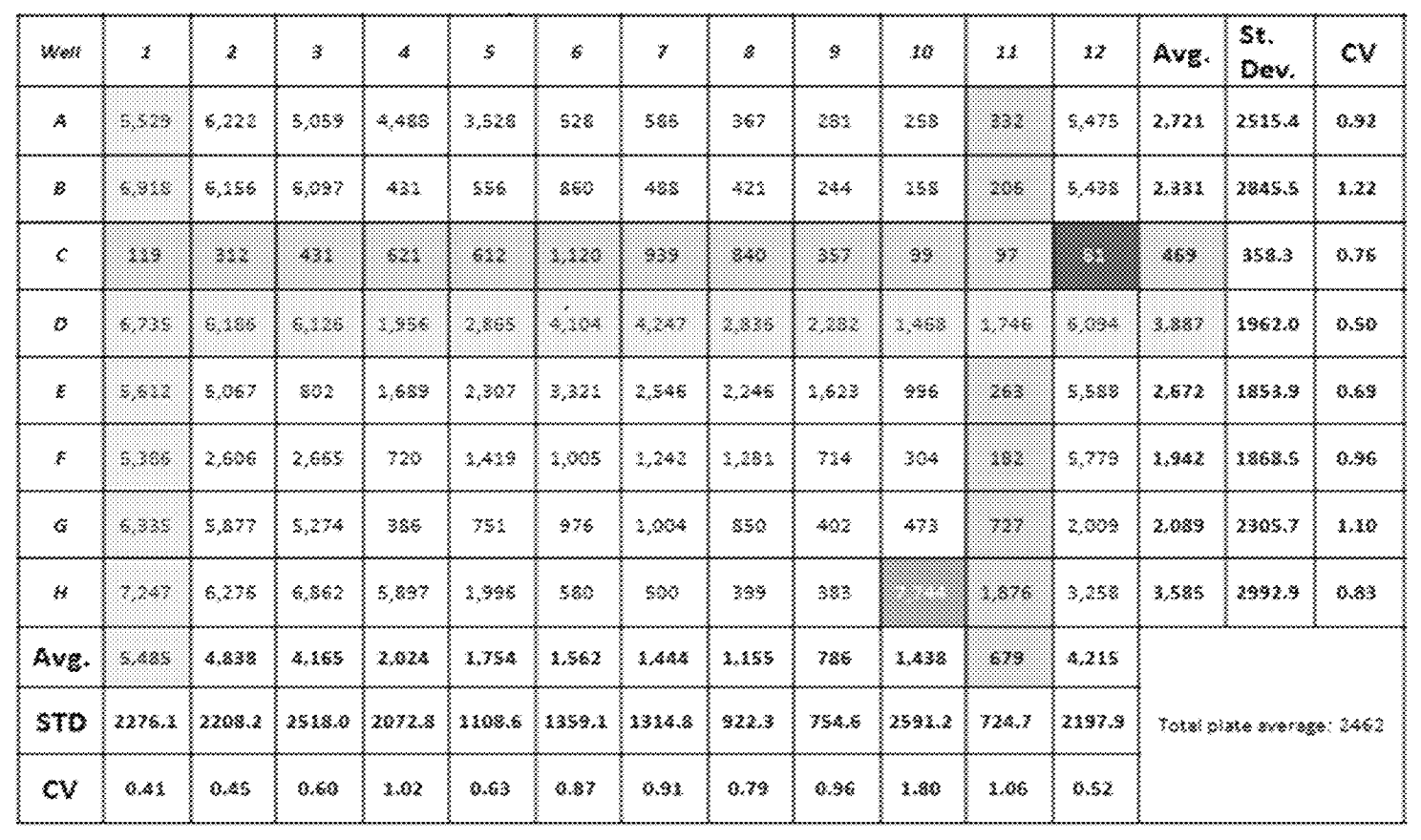

As shown in FIGS. 5-7, significant improvement to increasing particle counts across the entire multi-well plate has been achieved through a new approach of sample collection for flow cytometry. In particular, a method of collecting cells or particles from individual wells of a multi-well plate for use in flow cytometry system has been achieved. The method includes adding a suspension of cells to wells of the plate; and aspirating cells from different wells according to a collection pattern into a flow cytometer, wherein the collection pattern is a sequential ordering of wells beginning at a middle region of the multi-well plate and continuing towards an outer region of the multi-well plate. By altering the collection pattern to collect samples from the middle region of the plate first, particles at greatest risk of settling from solution can be collected prior to the settling occurring. Combining this collection pattern approach with rotating or shaking the multi-well plate to maintain the suspension of cells in outer wells surprisingly increased the consistency of particle counts across the entire plate. To this end, in preferred embodiments the method further includes rotating or agitating the multi-well plate between steps of aspirating cells from different wells, a least those along the outermost regions of the plate. The rotating or agitating can be performed using a rotating platform or shaking platform incorporated into a multi-well plate sampling chamber of a flow cytometer and the rotation or shaking feature can be programmed to occur between aspirating different wells. Further, the rotating or shaking platform can also be programmed to position the required well under an aspiration needle of a flow cytometer.

Although the examples demonstrate the improvements over the art with respect to particles and in particular to silica beads or polystyrene beads, the method is equally useful for cell analysis. The similarity of tested 5 µm polystyrene beads (Spheroteach Accucount Beads) to cells is depicted in FIG. 3, where the forward scatter (FSC) and side scatter (FSC) of the particles is depicted. The gated E1 and E2 populations match the parameters for human cells. Like particles, cells tend to settle from solution and collect at the bottom of multi-well plates. Further, it has also been observed that agitating or rotating multi-well plates is significantly more effective at suspending cells that are at end columns compared to middle columns and at end rows compared to middle rows when the plate is positioned at the middle of the rotating or shaking apparatus. As further guidance for the skilled artisan, the method will be useful when aspirating cells or particles sized between 0.2 µm to 150 µm. The skilled artisan will further appreciate that the method is useful for aspirating prokaryotic or eukaryotic cells and will have particular use for aspirating human cells, whether normal, infected with disease, cancerous cells or at any stage of development.

The skilled artisan will also appreciate that cells can be harvest from any suitable fluid or organ as known in the flow cytometry arts, such as blood, serum or tissue biopsy. Cells can be harvested from adipose tissue. Alternatively, the cells can be from cell lines as known in the art to which the invention belongs. To this end, the method can be used when detecting, counting or sorting any cell or particle population consistent with flow cytometry systems including cancer cells, monocytes, lymphocytes, and any other cells isolated from tissue or grown in cultures sized between 0.2 µm to 150 µm and suited for flow cytometry applications.

Although the methods herein significantly improve counts across the entire multi-well plate and significantly improve counts from the middle region of the multi-well plate, the methods may be optimized to achieve even greater consistency in particle or cell accounts. Among these modifications the user may wish to optimize the number of cells added to each well. That is, the artisan may find it beneficial to add fewer or more cells across the multi-well plate, although it is generally preferred to have the same number of cells in each well. Another modification may be to alter the volume in the well such as increasing the sample volume or decreasing the sample volume, which may depend on the concentration of cells in the well.

In some instances, cells will be added to the wells, aspirated according to the collection pattern and analyzed according to forward scatter (FSC) or side scatter (SSC) parameters. Such comparisons can be used to isolate monocyte populations from red blood cells. However, the skilled artisan will also appreciate that since flow cytometry often involves labelling cells with one or more binding reagents for fluorescent detection, the method will be especially useful in such procedures. Accordingly, prior to aspiration the cells may be labelled with one or more labelled binding reagents against one or more cell biomarkers or exposed to one or more detectable intercalating agents. Consistent with the flow cytometry arts, the labelled binding reagents can be fluorescently labelled antibodies or fluorescently labelled antibody fragments. There are many fluorescent labels from which the artisan may choose, of which flourescein (FITC), phycoerythrin (PE) and allophycocyanin (APC) tend to be very popular. However, research and development groups are continually developing new fluorochromes for the flow cytometry arts and thus the availability of corresponding labelled binding reagents are increasingly available through a variety of companies, including but not limited to Becton Dickenson (Franklin Lakes, N.J.), Jackson ImmunoResearch Laboratories, Inc (West Grove, Pa.) and many others known those skilled in the flow cytometry arts. Each of these can be used with the present invention. In some embodiments the intercalating agent is propidium idodide, which can intercalate into DNA molecules. Again, such molecules are also commonly known in the art to which the invention belongs and are included in the present invention.

In flow cytometry, cells are aspirated using an aspirating needle, which directs cells into the flow cytometer, where cells mix with sheath fluid and are streamed through a flow cell for excitation. As such, the invention is directed towards maximizing the availability of cells through the flow cell by provide new sample collection patterns that increase the consistency of cell counts or particle accounts across the multi-well plate. The term "collection pattern" as used herein refers to the sequence or order for aspirating wells across the multi-well plate for collection by the flow cytometer and thus streaming through the flow cell.

In some embodiments, the collection pattern may be ordered beginning with wells having a tendency to produce a lowest particle or cell count to wells having a tendency to produce a highest particle or cell count. This order can be determined experimentally by counting cells or particles across the multi-well plate over a series of experiments while agitating or rotating the plate. The wells can then be statistically ordered from lowest particle or cell count to highest particle or cell count and the order designated as a collection pattern for future sample collection.

Alternatively, the collection pattern can include groups of wells that are grouped according to count ranges then ordered such that groups with lower count ranges are aspirated before groups with higher count ranges. For example, a group of wells having a count range of 0-250 counts would precede a group of wells with a count range of 250-500 counts, which would precede a group of wells with a count range of 500-1000 counts. This approach may be preferred when count variation between wells within a same count range continually alter the aspiration sequence using an absolute lowest to highest ordering. That is, wells in a same region, such as the middle most region, may equally suffer from low cell or particle counts and therefore their relative ordering with each other may be less important compared to their ordering compared to wells of different regions on the multi-well plate.

In some embodiments, the collection pattern is a series of successive square patterns, where a first square pattern of wells is encircled by a second square pattern of wells, and so on. In such a pattern the order of aspirating wells in each square pattern may be randomly assigned or may be further ordered such as ordered clockwise or counterclockwise.

In some embodiments, the collection pattern is a spiral-square pattern, which is characterized as a series of successive square patterns that circle the middle region or a central well with a caveat that moving to a next well in the collection sequence is performed by aspirating a well that is adjacent (either horizontally adjacent, vertically adjacent, or diagonally adjacent) to the most recently aspirated well. An example is shown in FIG. 1, where a first square pattern is defined by the collection sequence 2-9 and a second square pattern is defined by the collection sequence 10-25, where moving outward from the first square pattern to the second square pattern occurs at adjacent wells E5 and F5, which are ordered as collection sequence numbers 9 and 10. The skilled artisan will appreciate that the outward movement could alternatively be performed between wells E5 and either wells D4, E4 or F4. Similarly, adjacent wells F4 and G4 in FIG. 1 are suited for the outward movement from the second square pattern (designated by order 10-25) to a successive third square pattern (designated by order 26-49); however outward movement could also have been performed between wells F4 and E3, F3 or G3. Also as shown in FIG. 1, when the multi-well plate is a 96 well plate, the spiral-square configuration can include three successive square patterns (e.g. defined by collection sequences 2-9, then 10-25, then 26-49) around a central well, in this case well D6. When determining a middle region to begin a collection pattern for a 96 well plate, the middle region or central well is preferably assigned to D6; however, any well between C5-C7, D5-D7 or E5-E7 of a 96 well plate may be assigned to the middle region or center well of a 96 well plate and thus designated as a first well in the collection pattern. The skilled artisan will appreciate these modifications would shift the row and column combination for the collection pattern but a same spiral-square pattern could still be followed. The artisan will also appreciate that the spiral-square pattern can spiral to the left or right.

The artisan will also appreciate that the above collection pattern can also be applied to multi-well plates having more or less than 96 wells. In such cases, the middle-most well can be chosen or chosen from a group of middle most wells, and the collection pattern followed.

In some instances a square collection pattern or spiral-square collection pattern cannot be followed throughout the entire multi-well plate because of the plate layout. That is, in some instances, such as that of FIG. 1, the multi-well plate is not dimensioned such that a successive square or square-spiral pattern can collect samples from all wells. In such instances it is advisable to incorporate at least a second pattern for aspirating outermost wells that cannot be collected using the first collection pattern. Such second patterns can be a rectangular pattern that does not encircle the center well (e.g. a pattern of collecting samples from column 2 followed by column 1 then column 11 followed by column 12 in a 96 well plate) or as shown in FIG. 1, a meandering pattern that moves sequentially between two neighboring columns along each row.

In an exemplary embodiment, the multi-well plate is a 96 well plate and the collection order follows the wells D6, E6, E7, D7, C7, C6, C5, D5, E5, F5, F6, F7, F8, E8, D8, C8, B8, B7, B6, B5, B4, C4, D4, E4, F4, G4, G5, G6, G7, G8, G9, F9, E9, D9, C9, B9, A9, A8, A7, A6, A5, A4, A3, B3, C3, D3, E3, F3, G3, H3, H4, H5, H6, H7, H8, H9, H10, G10, F10, E10, D10, C10, B10, A10. In one variation, the order further comprises A2, A1, B1, B2, C2, C1, D1, D2, E2, E1, F1, F2, G2, G1, H1, H2, H11, H12, G12, G11, F11, F12, E12, E11, D11, D12, C12, C11, B11, B12, A12, A11. In another variation, the order further comprises a second collection sequence alternating or meandering between column 1 and column 2 or column 11 and column 12.

Another embodiment is depicted in FIG. 2, where the collection pattern is a nearest to center pattern, where wells are ordered for aspiration by nearest proximity to a center of the multi-well plate independent of whether a well is positioned at the center of the multi-well plate. As shown in FIG. 2, the center of the multi-well plate is positioned at the intersection of wells D6, D7, E6 and E7. The collection pattern then begins from a nearest well to a farthest well, and where the order of wells that share a same distance (i.e. D6, D7, E6 and E7) can be interchanged. In another variation if wells are equidistant from the center of the multi-well plate the pattern may further include a caveat that the closest well to the well aspirated immediately prior to the query follows next.

An exemplary embodiment of a nearest to center collection pattern is shown in FIG. 2, where in a 96 well plate and the well aspiration order is D6, E6, E7, D7, C7, C6, D5, E5, F6, F7, E8, D8, C8, C5, F5, F8, E9, D9, B7, B6, D4, E4, G6, G7, G8, F9, C9, B8, B5, C4, F4, G5, H6, H7, E10, D10, A7, A6, D3, E3, G4, G9, B9, B4, C3, F3, H5, H8, F10, C10, A8, A5, A4, B3, G3, H4, H9, G10, B10, A9, D2, E2, E11, D11, C11, F11, F2, C2, A3, H3, H10, A10, B11, G11, G2, B2, D1, E1, E12, D12, C12, F12, F1, C1, A2, H2, H11, A11, B12, G12, G1, B1, A1, H1, H12, and A12.

As with prior embodiments, the nearest to center collection pattern can be combined with a second pattern that differs from the first. In such embodiments, preferably the nearest to center collection pattern is followed over the first 25% of wells, more preferably over first 50% of wells and still more preferably of the first 75% of wells.

Similarly, the symmetry of a multi-well plate may permit the collection pattern to proceed to the left or to the right, each of which is encompassed herein.

In other embodiments a collection pattern deviates less than 15% from one of the collection patterns disclosed, where the deviation from a collection pattern is determined by comparing the collection sequences and calculating the percent difference. If the percent difference is within 15 percent it is within the corresponding collection pattern.

Since collection patterns themselves are sets of ordered sequences, the collection patterns may be programmed by the user into a sample collection software module for use with a flow cytometer or can be provide as one or more collection presets in the flow cytometer, which provides the user with a selectable option to use one or more collection patterns. Alternatively, the sample collection module of sample acquisition software may automatically perform the collection patterns herein.

Collection patterns have been followed by adapting a currently available multi-sampling flow cytometry system, namely, the NOVOCYTE flow cytometer offered by ACEA BIOSCIENCES, INC. together with a sample collection software program. Depending on the adjustability of the user's flow cytometer system, the artisan may follow the disclosed patterns of sample collection to initiate suitable collection pattern programming. In other embodiments, software designers may preprogram software to collect samples according the patterns disclosed herein and optionally provide the user with one or more selectable options or patterns for sample collection. The skilled artisan will appreciate that the programming of collection patterns herein is not limited to any particular program language as programming could differ between flow cytometry systems. In some embodiments, the programming may adapt a Cartesian coordinate system where plots along perpendicularly aligned axes correspond to well locations.

EXAMPLES

Embodiments of the invention may be further understood in light of the following examples, which are not to be construed as limiting the scope of the disclosure in any way.

Example I

Significant Variability in Particle Count was Found Using Row-by-Row Collection Pattern for Flow Cytometry The inventions addresses inconsistencies in cell counts found to continually occur when using a row by row or column by column based method in sample acquisition. The following example demonstrates the inconsistencies found in wells across a 96 well plate when measuring cell counts using a row by row sample acquisition approach using the NOVOCYTE flow cytometer (ACEA Biosciences, Inc., San Diego, Calif.).

A suspension of silica beads was vortexed to ensure the beads were equally distributed throughout the solution. An equal volume of the suspension was aliquoted into each well of a 96 well plate to ensure an equal load across all wells. The NOVOCYTE flow cytometer (ACEA BIOSCIENCES, San Diego, Calif.) was programed to sequentially acquire 10 uL of sample from each well and count the silica beads in each acquired sample. Between acquiring samples from each well, the plate was subjected to rotation or agitation for 15 seconds using a shaking platform. The pattern of sample acquisition followed a row by row sequence, which acquires samples sequentially from columns 1-12 of row A, followed by acquiring samples sequentially from columns 1-12 of row B, followed by acquiring samples sequentially from columns 1-12 of row C, followed by acquiring samples sequentially from columns 1-12 of row D, followed by acquiring samples sequentially from columns 1-12 of row E, followed by acquiring samples sequentially from columns 1-12 of row F, followed by acquiring samples sequentially from columns 1-12 of G, and finally followed by acquiring samples sequentially from columns 1-12 of row H.

The total counts for each well were recorded and are reproduced in FIG. 4. In addition, samples across each row and down each column of the multi-plate were analyzed to determine the average per well count (Avg.), the standard deviation (St. Dev.) and coefficient of variation (CV). In addition the well average from the entire plate was also determined.

As shown in FIG. 4, the results show that far fewer particles were detected from samples collected from center wells compared to those around the edges. For example, wells D7, E6, E7, F5-7, and G4-8 produced zero counts, whereas columns 1, 2 and 10-12 each averaged over 1000 counts. The absence of counts is likely to have occurred by particles settling to the bottom of the wells even after rotating or agitating the multi-well plate. The average count across the entire plate was 891.

Example II

Improved Sample Consistency Found when Acquiring Samples Using a Spiral-Square Approach The following example demonstrates improved consistency in particle counts across the multi-well plate when acquiring samples using a spiral-square approach.

A suspension of silica beads was vortexed to ensure the beads were equally distributed throughout the solution. An equal volume of the suspension was aliquoted into each well of a 96 well plate to ensure an equal load across all wells. The NOVOCYTE flow cytometer (ACEA BIOSCIENCES, San Diego, Calif.) was programed to sequentially acquire 10 uL of sample from each well and count the silica beads in each acquired sample. Between acquiring samples from each well, the plate was subjected to rotation or agitation for 15 seconds. The pattern of sample acquisition followed a spiral-square configuration using the following order. D6, E6, E7, D7, C7, C6, C5, D5, E5, F5, F6, F7, F8, E8, D8, C8, B8, B7, B6, B5, B4, C4, D4, E4, F4, G4, G5, G6, G7, G8, G9, F9, E9, D9, C9, B9, A9, A8, A7, A6, A5, A4, A3, B3, C3, D3, E3, F3, G3, H3, H4, H5, H6, H7, H8, H9, H10, G10, F10, E10, D10, C10, B10, A10, A2, A1, B1, B2, C2, C1, D1, D2, E2, E1, F1, F2, G2, G1, H1, H2, H11, H12, G12, G11, F11, F12, E12, E11, D11, D12, C12, C11, B11, B12, A12, A11.

The total counts for each well were recorded and are reproduced in FIG. 5. In addition, samples across each row and down each column of the multi-plate were analyzed to determine the average per well count (Avg.), the standard deviation (St. Dev.) and coefficient of variation (CV). In addition the well average from the entire plate was also determined.

As shown in FIG. 5, the results show more consistent particle counts across the entire plate compared to the row-by-row approach of Example I and no well had zero counts. Further, the average particle count across the plat was 2672, which is a significant improvement of the results from Example 1.

Example III

Improved Sample Consistency Found when Acquiring Samples Using a Nearest Well to Center Approach The following example demonstrates improved consistency in particle counts across the multi-well plate when acquiring samples using a nearest well to center approach.

A suspension of silica beads was vortexed to ensure the beads were equally distributed throughout the solution. An equal volume of the suspension was aliquoted into each well of a 96 well plate to ensure an equal load across all wells. The NOVOCYTE flow cytometer (ACEA BIOSCIENCES, San Diego, Calif.) was programed to sequentially acquire 10 uL of sample from each well and count the silica beads in each acquired sample. Between acquiring samples from each well, the plate was subjected to rotation or agitation for 15 seconds. The pattern of sample acquisition followed a nearest well to center configuration using the following order. D6, E6, E7, D7, C7, C6, D5, E5, F6, F7, E8, D8, C8, C5, F5, F8, E9, D9, B7, B6, D4, E4, G6, G7, G8, F9, C9, B8, B5, C4, F4, G5, H6, H7, E10, D10, A7, A6, D3, E3, G4, G9, B9, B4, C3, F3, H5, H8, F10, C10, A8, A5, A4, B3, G3, H4, H9, G10, B10, A9, D2, E2, E11, D11, C11, F11, F2, C2, A3, H3, H10, A10, B11, G11, G2, B2, D1, E1, E12, D12, C12, F12, F1, C1, A2, H2, H11, A11, B12, G12, G1, B1, A1, H1, H12, A12.

The total counts for each well were recorded and are reproduced in FIG. 6. In addition, samples across each row and down each column of the multi-plate were analyzed to determine the average per well count (Avg.), the standard deviation (St. Dev.) and coefficient of variation (CV). In addition the well average from the entire plate was also determined.

As shown in FIG. 6, the results show more consistent particle counts across the entire plate compared to the row-by-row approach of Example 1 and no well had zero counts. Further, the average particle count across the plat was 2462, which is a significant improvement of the results from Example 1.

Example IV

Improved Sample Consistency Found when Acquiring Samples Under Reduced Loads Using a Spiral-Square Approach Since the above examples demonstrated improved consistency across the entire plate compared to the row-by-row approach, the spiral-square approach was also tested with reduced loads.

A suspension 5 µm polystyrene beads (Spherotech Accucount Beads) was vortexed to ensure the beads were equally distributed throughout the solution. An equal volume of the suspension was aliquoted into each well of a 96 well plate to ensure an equal load across all wells. The NOVOCYTE flow cytometer (ACEA BIOSCIENCES, San Diego, Calif.) was programed to sequentially acquire 10 uL of sample from each well and count the silica beads in each acquired sample. Between acquiring samples from each well, the plate was subjected to rotation or agitation for 15 seconds. The pattern of sample acquisition followed a spiral-square configuration using the following order. D6, E6, E7, D7, C7, C6, C5, D5, E5, F5, F6, F7, F8, E8, D8, C8, B8, B7, B6, B5, B4, C4, D4, E4, F4, G4, G5, G6, G7, G8, G9, F9, E9, D9, C9, B9, A9, A8, A7, A6, A5, A4, A3, B3, C3, D3, E3, F3, G3, H3, H4, H5, H6, H7, H8, H9, H10, G10, F10, E10, D10, C10, B10, A10, A2, A1, B1, B2, C2, C1, D1, D2, E2, E1, F1, F2, G2, G1, H1, H2, H11, H12, G12, G11, F11, F12, E12, E11, D11, D12, C12, C11, B11, B12, A12, A11.

The total counts for each well were recorded and are reproduced in FIG. 7. In addition, samples across each row and down each column of the multi-plate were analyzed to determine the average per well count (Avg.), the standard deviation (St. Dev.) and coefficient of variation (CV). In addition the well average from the entire plate was also determined.

As shown in FIG. 7, the results show more consistent particle counts across the entire plate compared to the row-by-row approach of Example 1. A sampling error occurred in A5, which resulted in zero counts. Variation between columns and rows was found to be at most 5%, which is much lower than the variation found in Example 1.

The detailed description set-forth above is provided to aid those skilled in the art in practicing the present invention. However, the invention described and claimed herein is not to be limited in scope by the specific embodiments herein disclosed because these embodiments are intended as illustration of exemplary improvements of the invention. Any equivalent embodiments are intended to be within the scope of this invention. Indeed, various modifications of the invention in addition to those shown and described herein will become apparent to those skilled in the art from the foregoing description which do not depart from the spirit or scope of the invention. Such modifications are also intended to fall within the scope of the appended claims.

What is claimed is:

1. A method of collecting cells from individual wells of a multi-well plate for use in flow cytometry, the method comprising:
adding a suspension of cells to wells of the multi-well plate; and
aspirating cells from different wells according to a collection pattern into a flow cytometer, wherein the collection pattern is a sequential ordering of wells beginning at a middle region of the multi-well plate and continuing towards an outer region of the multi-well plate.

2. The method according to claim 1, wherein the multi-well plate is a 96 well plate, characterized as having rows A-H and columns 1-12, further wherein the middle region is characterized as a well selected from the group consisting of wells D6, D7, E6 and E7.

3. The method according to claim 2, wherein cells from wells B4-B8, C4-C8, D4-D8, and E4-E8 are aspirated before cells from all remaining wells.

4. The method according to claim 2, wherein cells from wells C5-C7, D5-D7, and E5-E7 are aspirated before cells from all remaining wells.

5. The method according to claim 1, wherein the collection pattern is a spiral-square pattern, which is characterized as a series of wells in successive square patterns that each circle the middle region and where the sequential ordering proceeds by aspirating adjacent wells.

6. The method according to claim 5, wherein the multi-well plate is a 96 well plate and the spiral-square pattern comprises three successive square patterns around a central well.

7. The method according to claim 1, wherein the pattern is a square pattern of at least three successive squares around a central well.

8. The method according to claim 1, wherein the multi-well plate is a 96 well plate characterized as having rows A-H and columns 1-12, further wherein the sequential ordering comprises the order D6, E6, E7, D7, C7, C6, C5, D5, E5, F5, F6, F7, F8, E8, D8, C8, B8, B7, B6, B5, B4, C4, D4, E4, F4, G4, G5, G6, G7, G8, G9, F9, E9, D9, C9, B9, A9, A8, A7, A6, A5, A4, A3, B3, C3, D3, E3, F3, G3, H3, H4, H5, H6, H7, H8, H9, H10, G10, F10, E10, D10, C10, B10, and A10.

9. The method according to claim 8, wherein the sequential ordering further comprises the order A2, A1, B1, B2, C2, C1, D1, D2, E2, E1, F1, F2, G2, G1, H1, H2, H11, H12, G12, G11, F11, F12, E12, E11, D11, D12, C12, C11, B11, B12, A12, A11.

10. The method according to claim 8, wherein the sequential ordering further comprises alternating between wells of column 1 and wells of column 2 or wells of column 11 and wells of column 12.

11. The method according to claim 1, wherein the collection pattern is a nearest well to center pattern, which is characterized as successively aspirating cells from wells that are nearest to the middle region, further wherein the middle region is defined as a center of the multi-well plate independent of whether a well is positioned at the center.

12. The method according to claim 1, wherein the multi-well plate is a 96 well plate characterized as having rows A-H and columns 1-12 and the sequential ordering comprises the order D6, E6, E7, D7, C7, C6, D5, E5, F6, F7, E8, D8, C8, C5, F5, F8, E9, D9, B7, B6, D4, E4, G6, G7, G8, F9, C9, B8, B5, C4, F4, G5, H6, H7, E10, D10, A7, A6, D3, E3, G4, G9, B9, B4, C3, F3, H5, H8, F10, C10, A8, A5, A4, B3, G3, H4, H9, G10, B10, A9, D2, E2, E11, D11, C11, F11, F2, C2, A3, H3, H10, A10, B11, G11, G2, B2, D1, E1, E12, D12, C12, F12, F1, C1, A2, H2, H11, A11, B12, G12, G1, B1, A1, H1, H12, and A12.

13. The method according to claim 1, wherein the method further comprises aspirating cells from wells according to a second collection pattern on the same multi-well plate from remaining wells from which samples were not collected according to the initial collection pattern of claim 1.

14. The method according to claim 13, wherein the second collection pattern is a meandering pattern between two columns of wells.

15. The method according to claim 1, wherein the collection pattern is a selectable preset on flow cytometry software.

16. The method according to claim 1, further comprising labeling the cells with labelled binding reagents against one or more cell biomarkers.

17. The method according to claim 16, wherein the labelled binding reagents are fluorescently labelled antibodies or antibody fragments.

18. The method according to claim 1, further comprising rotating or agitating the multi-well plate between steps of aspirating cells from different wells.

* * * * *